United States Patent [19]

Koch et al.

[11] Patent Number: 5,192,322
[45] Date of Patent: Mar. 9, 1993

[54] IMPLANT FOR A PROSTHETIC LIGAMENT AND/OR TENDON REPLACEMENT

[75] Inventors: Rudolf Koch, Berlingen; Stefan Freudiger, Bremgarten; Hans Fluckiger, Oetwil, all of Switzerland

[73] Assignees: Sulzer Brothers Limited, Winterthur; Protek AG, Berne, both of Switzerland

[21] Appl. No.: 621,299

[22] Filed: Dec. 3, 1990

[30] Foreign Application Priority Data

Jan. 8, 1990 [CH] Switzerland .............................. 46/90

[51] Int. Cl.$^5$ ................................................ A61F 2/08
[52] U.S. Cl. ................................................ 623/13
[58] Field of Search .......................................... 623/13

[56] References Cited

U.S. PATENT DOCUMENTS

| | | | |
|---|---|---|---|
| 3,971,670 | 7/1976 | Homsy | 623/13 |
| 4,209,859 | 7/1980 | Hoffman | 3/1 |
| 4,663,886 | 5/1987 | Moorse et al. | 623/13 |
| 5,004,474 | 4/1991 | Fronk et al. | 623/13 |

FOREIGN PATENT DOCUMENTS

| | | |
|---|---|---|
| 0106501 | 4/1984 | European Pat. Off. ............. 623/13 |
| 0126520 | 11/1984 | European Pat. Off. . |
| 2278313 | 2/1976 | France . |
| WO89/01320 | 2/1989 | World Int. Prop. O. . |

*Primary Examiner*—Randy C. Shay
*Attorney, Agent, or Firm*—Kenyon & Kenyon

[57] ABSTRACT

The implant may be used as prosthetic replacement for a ligament and/or tendon. The implant has a plurality of discrete longitudinal strands disposed in side-by-side relation with transverse filaments about the strands. Individual sub-zones of the ligament are folded over in a transverse manner about a longitudinal axis of the sub-zone with intermediate zones being in an unfolded state. The intermediate zones may be formed solely of longitudinal strands to enhance flexibility.

9 Claims, 3 Drawing Sheets

IMPLANT FOR A PROSTHETIC LIGAMENT AND/OR TENDON REPLACEMENT

This invention relates to an implant for a prosthetic ligament and/or tendon replacement.

Heretofore, various types of implants have been known for the replacements of ligaments and tendons. For example, U.S. Pat. Nos. 4,242,660; 4,187,558 and 3,513,484 describe prosthetic implants formed of flat plane structures which are aligned substantially two dimensionally. For example, such structures have had longitudinally extending filament strands comprised of a number of discrete filaments strengthened, for example. by twisting or braiding or cabling with the filament strands being consolidated at least in parts of their length by transverse filaments.

When implants of this kind are stressed in bending, for example, at the edge of a fixing bore, some of the longitudinal filaments experience tension while others compression. On the other hand, natural ligaments, which are also built up from individual longitudinally extending fibers, are three-dimensional "structures" which are combined from crossing fiber bunches and which are stressed in loading solely in tension, none of them experiencing compression, one or a few bunches dealing with the "main-load" initially and other bunches coming into action as loads and stretches increase.

French Patent 2,278,313 describes various types of synthetic tendons which are constructed with end parts having various constructions to permit bending and anchorage.

European Patent Application 0126520 describes a prosthetic ligament which is comprised of an elongate forminous flexible strip.

WO 89/01320 describes a soft tissue prosthesis which is constructed in cable-like manner. In one portion of the prosthesis, a central region is composed of individually braided tubes while adjacent regions are formed of braided fabric to encase the braided tubes therein.

U.S. Pat. No. 4,209,859 describes a ligament and tendon prosthesis of tubular construction throughout.

Accordingly, it is an object of the invention to provide an implant as a replacement for ligaments and/or tendons whose operation simulates to a very considerable extent the operation of the anatomy and the physiology of a natural ligament or tendon.

It is another object of the invention to provide an implant of relatively simple construction which can be readily manipulated into place in the anatomy.

Briefly, the invention provides an implant for a prosthetic replacement of one of a ligament and tendon comprising a plurality of discrete longitudinal strands disposed in side-by-side parallel relation, with the strands being disposed to define a pair of axially spaced apart transversely folded-over sub-zones and a central zone between the sub-zones. In addition, the implant has transverse filaments disposed about at least some of the strands in each sub-zone to reinforce the strands.

The implant also has means for securing the strands in each sub-zone in folded-over relation at longitudinally spaced apart points. In this respect, the strands may be disposed in overlapping relation in each sub-zone and the strands of each respective sub-zone may be folded over in an opposite direction to the strands of the other sub-zone.

The folding of discrete sub-zones deforms the implant into a three-dimensional member in which, in response to natural loading of the band and given adequate prestressing, the longitudinally extending fiber strands experience only tension and no compression.

To achieve a crossing of at least individual ones of the longitudinal strands, the central zone between the two folded zones of the implant has only longitudinally extending filament strands. This crossing of the strands can be further boosted if the folded zones adjoining the part consisting solely of longitudinally extending strands are twisted relatively to one another in opposite directions around their longitudinal axis.

Another advantage of the implant is that the folding facilitates implantation through a bore in the bone and fixing thereto. It may be advantageous in this case if the folded zone are "rolled" -i.e., if the lateral edges of the latter zones overlap over another.

An approximation of the operation of the synthetic ligament to the operation of a natural ligament can be further enhanced if two consecutive folded zones of the parts are folded in opposite directions.

The looping or the like of transverse filaments around the longitudinal strands can be effected in a manner known for the production of flat textile structures or bands, for example, by weaving, braiding, knitting or the like.

These and other objects and advantages of the invention will become more apparent from the following detailed description taken in conjunction with the accompanying drawings wherein.

Figure 1:
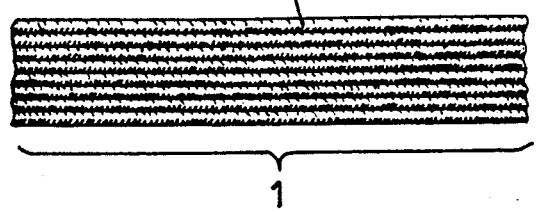
FIG. 1 illustrates a plan view of a part of a ligament prosthesis in an unfolded state with the part reinforced by transverse filaments in accordance with the invention.

Referring to FIG. 1, a part 1 of an implant is formed of discrete longitudinal filaments 2 (see FIG. 2) which are consolidated by transverse filaments 3 to form a stable flat band-like textile structure. Each strand 2 comprises a number of discrete filaments which can be formed into the strand 2 by braiding. Other methods known from textile technology, such as twisting or cabling can, of course, be used to combine a number of discrete filaments into a filament strand 2. The transversely reinforced part 1 of the implant can be produced by weaving as well as by other textile production methods, such as braiding or knitting.

Figure 2:
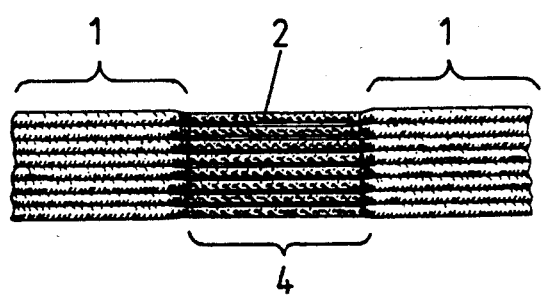
FIG. 2 illustrates a plan view of a part of an implant having a pair of reinforced sub-zones and an unreinforced central zone in accordance with the invention.
Figure 3:
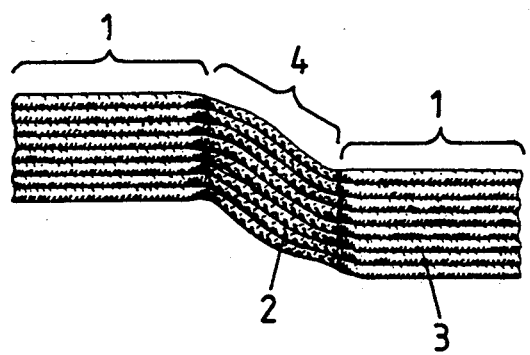
FIG. 3 illustrates a view similar to FIG. 2 to demonstrate the transverse resilience and flexibility of the ligament prosthesis of FIG. 2.

Referring to FIG. 2, wherein like reference characters indicate like parts as above, the implant may have transversely reinforced parts 1 separated from one another by a part 4 consisting solely of longitudinally extending filaments strands 2. As indicated in FIG. 3, the part 4 between the two reinforced parts 1 enhances the flexibility of the implant.

The filaments for the strands 2 and the transverse filaments 3 may preferably be made of polyester and polythene.

Figure 4:
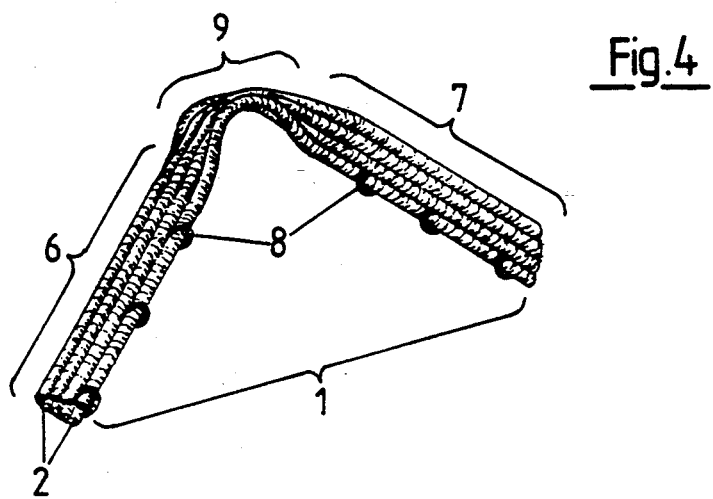
FIG. 4 illustrates the implant of FIG. 1 with two sub-zones folded in the same direction with an unfolded central zone in accordance with the invention.

Referring to FIG. 4, wherein like reference characters indicate like parts as above, in order to approximate the operation of a natural ligament, axially spaced apart sub-zones 6, 7 of the transversely reinforced part 1 of the ligament of FIG. 1 are folded. As illustrated, the strands 2 of each sub-zone 6, 7 are transversely folded-over about a longitudinal axis in each sub-zone 6, 7. Means are also provided for securing the strands 2 in each sub-zone 6, 7 in folded-over relation. This means may serve to secure the folded-over sub-zone 6, 7 by local or continuous connection for example, by sewing together of the lateral edges of the sub-zones 6, 7 at spaced apart points 8.

As indicated in FIG. 4, the sub-zones 6, 7 are folded in the same direction. In addition, an operative central zone 9 is disposed between the sub-zones 6, 7 which is flexible. The folded zone 6, 7 are very often drawn into bores in a bone whereas, for example, the central zone 9 is disposed in an intra-articular space of the joint having the ligament prosthesis.

The means for securing the lateral edges of the folded sub-zone 6, 7 may be affected in other ways than by sewing. For example, securement can be affected by having the lateral edges adhered or welded together.

Figure 5:
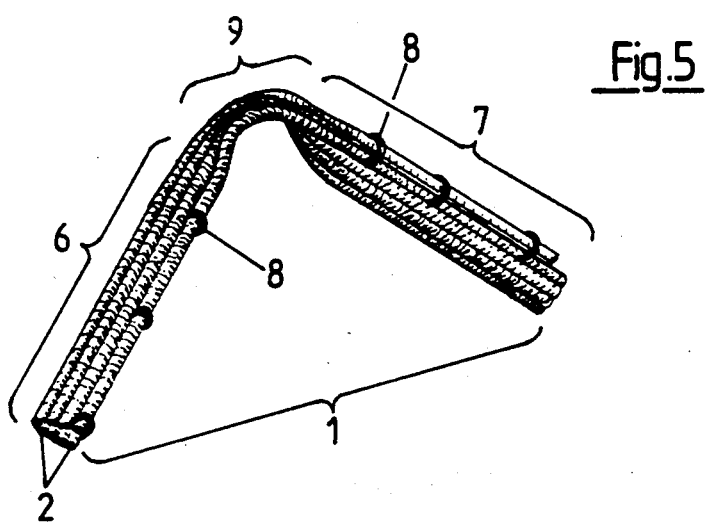
FIG. 5 illustrates a view similar to FIG. 4 of a ligament with two sub-zones folded in opposite directions.

Referring to FIG. 5, wherein like reference characters indicate like parts as above, the folded over sub-zone 6, 7 may be folded in opposite directions to each other.

Figure 6:
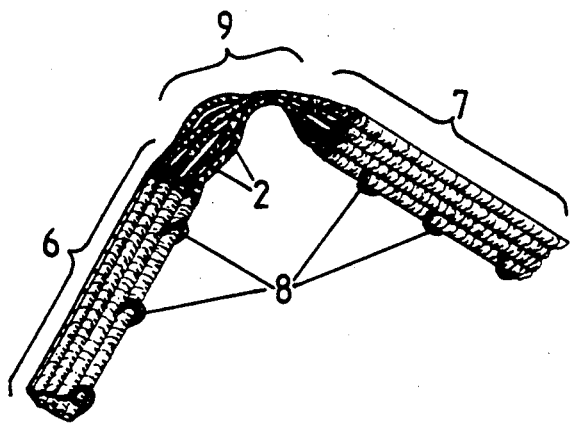
FIG. 6 illustrates a view of the implant of FIG. 2 with two sub-zones folded in the same direction.
Figure 7:
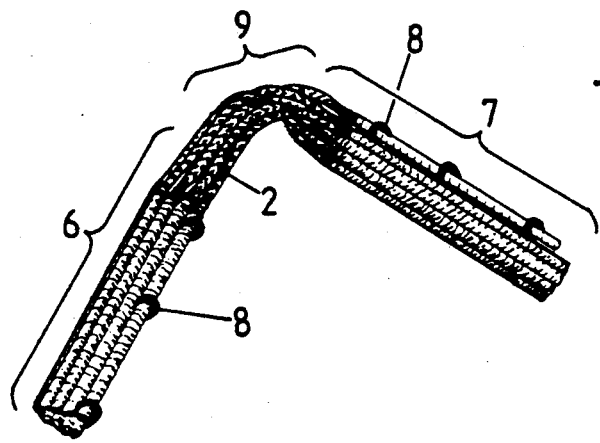
FIG. 7 illustrates sa view similar to FIG. 6 of an implant having sub-zones folded in opposite directions in accordance with the invention.

Referring to FIG. 6, wherein like reference characters indicate like parts as above, when the parts of a ligament prosthesis as illustrated in FIG. 2 are folded, an operative central zone 9 is formed by the part 4 (see FIG. 2) which consists solely of longitudinally extending strands 2. A synthetic ligament is therefore provided which has a very flexible operative zone in which the discrete strands 2, by being unsecured relative to each other, are displacable relative to one another and can therefore cross over one another to some extent as illustrated. As indicated in FIG. 4, the sub-zone 7 of the implant can be folded over in the same direction relative to a longitudinal axis passing therethrough. Alternatively, as illustrated in FIG. 7, the sub-zones may be folded over in opposite directions relative to the respective longitudinal axis.

Figure 8:
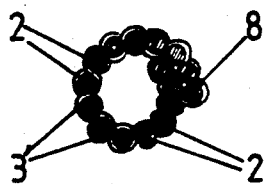
FIG. 8 illustrates a cross-section-through a folded zone of an implant with lateral edges disposed in overlapping relation in accordance with the invention.

Referring to FIG. 8, the folding over of the implant zones can be executed so that the lateral edges of a part 1 overlap in the folded over zone. In this way, the folded zones acquire increased rigidity and have their diameter reduced, thus facilitating, more particularly, the pulling of the implant into or through a bore in a bone.

The unfolded flexible operative zone 9 of the implant which remains between the folded sub-zones 6, 7 can be deformed during movements of a joint in which the implant is implanted.

Folding of the sub-zones of the implant imparts to the basically two-dimensional plane implant a shape which approximates the shape of a natural ligament and ensures that the longitudinally extending yarn strands 2 experience only tension when loaded while individual strands 2 do not experience compression. This feature approximates that of a natural ligament.

The invention thus provides an implant which can be used as a prosthetic replacement for a ligament and/or a tendon in which the individual strands of the implant need not be subjected to compression within a bend. In this respect, the invention provides an implant which closely simulates that of a natural ligament or tendon, as the case may be.

What is claimed is:

1. An implant for a prosthetic replacement of one of a ligament and tendon comprising
   a plurality of discrete longitudinal strands disposed in side-by-side parallel relation, said strands defining a pair of axially spaced apart sub-zones, each sub-zone being folded over about a longitudinal axis, and a central zone between said sub-zones, wherein each longitudinal strand is free to move relative to each other longitudinal strand within said central zone; and
   transverse filaments disposed about at least some of said strands of each sub-zone to reinforce said strands.

2. An implant as set forth in claim 1 which further has means for securing said strands in each sub-zone in folded-over relation at longitudinally spaced apart points.

3. An implant as set forth in claim 1 wherein said central zone is formed solely of said strands.

4. An implant as set forth in claim 1 wherein said strands are disposed in overlapping relation in each sub-zone.

5. An implant for a prosthetic replacement of one of a ligament and tendon comprising
   a plurality of discrete longitudinal strands defining a pair of axially spaced apart sub-zones, each sub-zone being folded over about a longitudinal axis, and a central zone between said sub-zones, wherein said strands are disposed in side-by-side parallel relation within each sub-zone, and wherein said strands are folded over about the longitudinal axis in opposite directions in said respective sub-zones; and
   transverse filaments disposed about at least some of said strands of each sub-zone to reinforce said strands.

6. An implant for one of a ligament and a tendon replacement having a pair of axially spaced apart sub-zones and a central zone between said sub-zones, a plurality of discrete longitudinal strands secured in parallel relation within said sub-zones and wherein each strand is free to move relative to each other longitudinal strand within the central zone, said strands extending through said sub-zones and said central zone, each sub-zone being folded over about a longitudinal axis such that said strands are disposed circumferentially about said longitudinal axis in each sub-zone, and transverse filaments disposed about at least some of said strands in each sub-zone to reinforce said strands.

7. An implant as set forth in claim 6 which further has means for securing said strands in each sub-zone in folded-over relation at longitudinally spaced apart points.

8. An implant for one of a ligament and a tendon replacement having a pair of axially spaced apart sub-zones and a central zone between said sub-zones, a plurality of discrete strands secured in parallel relation within said sub-zones and extending through said sub-zones and said central zone, said strands being disposed circumferentially about a longitudinal axis in each sub-zone, and transverse filaments disposed about at least some of said strands in each sub-zone to reinforce said strands, wherein said strands are folded over about the longitudinal axis in opposite directions in said respective sub-zones.

9. An implant for a prosthetic replacement of one of a ligament and tendon comprising a plurality of discrete longitudinal strands disposed in side-by-side parallel relation, said strands defining a pair of axially spaced apart sub-zones, each sub-zone being folded over a longitudinal axis, and a central zone between said sub-zones, said strands in said central zone being free to cross over one another and wherein each longitudinal strand is free to move relative to each other longitudinal strand within said central zone; and transverse filaments disposed about at least some of said strands of each sub-zone to reinforce said strands.

* * * * *

UNITED STATES PATENT AND TRADEMARK OFFICE
CERTIFICATE OF CORRECTION

PATENT NO. : 5,192,322

DATED : March 9, 1993

INVENTOR(S) : Koch et al.

It is certified that error appears in the above-indentified patent and that said Letters Patent is hereby corrected as shown below:

Abstract, line 1, after "as" insert --a--;

Column 2, line 17, change "zone" to --zones--;

line 49, change "sa" to --a--;

Column 6, line 2, after "over" insert --about--.

Signed and Sealed this

Third Day of May, 1994

*Attest:*

BRUCE LEHMAN

*Attesting Officer        Commissioner of Patents and Trademarks*